(12) United States Patent
Schlaf

(10) Patent No.: US 6,835,613 B2
(45) Date of Patent: Dec. 28, 2004

(54) METHOD OF PRODUCING AN INTEGRATED CIRCUIT WITH A CARBON NANOTUBE

(75) Inventor: Rudiger Schlaf, Lutz, FL (US)

(73) Assignee: University of South Florida, Tampa, FL (US)

( * ) Notice: Subject to any disclaimer, the term of this patent is extended or adjusted under 35 U.S.C. 154(b) by 47 days.

(21) Appl. No.: 10/313,886

(22) Filed: Dec. 6, 2002

(65) Prior Publication Data

US 2003/0157744 A1 Aug. 21, 2003

Related U.S. Application Data

(60) Provisional application No. 60/319,026, filed on Dec. 6, 2001, provisional application No. 60/319,182, filed on Apr. 12, 2002, and provisional application No. 60/319,183, filed on Apr. 12, 2002.

(51) Int. Cl.[7] ......................................... H01L 21/8238
(52) U.S. Cl. ..................... 438/199; 438/151; 438/618; 438/680
(58) Field of Search .......................... 438/20, 149, 151, 438/197, 199, 618, 99, 585, 680, 681

(56) References Cited

U.S. PATENT DOCUMENTS

| | | | |
|---|---|---|---|
| 6,146,227 A | 11/2000 | Mancevski | |
| 6,221,154 B1 | 4/2001 | Lee et al. | |
| 6,232,706 B1 | 5/2001 | Dai et al. | |
| 6,278,231 B1 | 8/2001 | Iwasaki et al. | |
| 6,322,713 B1 | 11/2001 | Choi et al. | |
| 6,325,909 B1 | 12/2001 | Li et al. | |
| 6,331,209 B1 | 12/2001 | Jang et al. | |
| 6,346,189 B1 | 2/2002 | Dai et al. | 205/766 |
| 6,445,006 B1 * | 9/2002 | Brandes et al. | 257/76 |
| 6,451,175 B1 | 9/2002 | Lal | |
| 6,457,350 B1 | 10/2002 | Mitchell | 73/105 |
| 6,492,261 B2 * | 12/2002 | Gavish et al. | 438/637 |
| 2003/0059968 A1 * | 3/2003 | Cheng et al. | 438/20 |
| 2003/0143327 A1 * | 7/2003 | Schlaf et al. | 427/249.1 |

FOREIGN PATENT DOCUMENTS

EP 1129990 * 5/2001

OTHER PUBLICATIONS

Publication: "Growth of a Single Freestanding Multiwall Carbon Nanotube On Each Nanonickel Dot"; published in Applied Physics Letters, vol. 75, No. 8, dated Aug. 23, 1999.
Publication: "High–Yield Assembly Of Individual Single–Walled Carbon Nanotube Tips For Scanning Probe Microscopies"; published in The Journal Of Physical Chemistry B, vol. 105, No. 4, Feb. 1, 2001.
Paper on "AFM and STM Investigation Of Carbon Nanotubes Produced By High Energy Ion Irradiation Of Graphite"; Journal Name: Nuclear Instruments & Methods In Physics Research, Section B (Beam Interactions with Materials and Atoms), Jan. 1, 1999, vol. 147, No. 1–4, Corporate Author—Res. Inst. For Tech. Phys. & Mater. Sci., Budapest Hungary.

(List continued on next page.)

*Primary Examiner*—Carl Whitehead, Jr.
*Assistant Examiner*—Thanhha Pham
(74) *Attorney, Agent, or Firm*—Howard & Howard

(57) ABSTRACT

A method of producing an integrated circuit with a carbon nanotube is disclosed. The integrated circuit includes a source, a drain, and a gate, and the source and the drain are positioned on the gate. A catalytic material is deposited onto the source. The catalytic material is then subjected to chemical vapor deposition. This initiates growth of the carbon nanotube such that the carbon nanotube extends from the source. Next, the carbon nanotube is bent toward the integrated circuit such that the carbon nanotube extends between the source and the drain to render the circuit operable.

17 Claims, 2 Drawing Sheets

OTHER PUBLICATIONS

Paper on "Electrical Transport In Pure And Boron–Doped Carbon Nanotubes", Journal Name: Applied Physics Letters, May 24, 1999, vol. 74, No. 21, Corporate Author—Inst. fur Metallkunde, Stuttgart Univ., Germany.

Paper on "Chemical Vapor Deposition Of Novel Carbon materials"; Journal Name: Thin Solid Films, Jun. 15, 2000, vol. 368, No. 2, Corporate Author—Dept. of Phys., Univ. of Central Florida, Orlando, FL, USA.

Paper on "Temperature Dependence Of The Resistivity Of Individual Multi–Walled Pure/Boron Doped Carbon Nanotubes At Elevated Temperatures"; Journal Name: AIP Conference Proceedings, 1999, vol. 486, pp. 371–374, Corporate Author—Max–Planck–Inst. fur Metallforschung, Stuttgart, Germany.

Paper on "Synthesis And Characterization of B(X)C(Y)N(Z) Nanotubes (Boron Carbonitride, Young's Modulus)", 1996, vol. 58–02B, pp. 762, Corporate Author—University of California, Berkeley.

Paper on "High–Yield Assembly Of Individual Single–Walled Carbon Nanotube Tips for Scanning Probe Microscopies"; Journal Name: Journal of Physical Chemistry B, Feb. 1, 2001, vol. 105, No. 4, Corporate Author—Dept. of Chem. & Chem. Biol., Harvard Univ., Cambridge, MA, USA.

U.S. Appl. No. 10/310,219, filed Dec. 5, 2002.
U.S. Appl. No. 10/413,597, filed Apr. 14, 2003.
U.S. Appl. No. 10/413,621, filed Apr. 14, 2003.
U.S. Appl. No. 10/413,598, filed Aug. 5, 2004.

Chin Li Cheung, Jason H. Hafner, Teri W. Odom, Kyoungha Kim, and Charles M. Lieber, "Growth and fabrication with single–walled carbon nanotube probe microscopy tips"; May 22, 2000; American Institute of Physics, Applied Physics Letters, vol. 76, No. 21, pp. 3136–3138.

Chin Li Cheung, Jason H. Hafner, and Charles M . Lieber, "Carbon nanotube atomic force microscopy tips: Direct growth by chemical vapor deposition and application to high–resolution imaging"; Apr. 11, 2000, PNAS, vol. 97, No. 8, pp. 3809–3813.

Hongjie Dia, Jason H. Hafner, Andrew G. Rinzler, Daniel T. Colbert, and Richard E. Smalley, "Nanotubes as Nanoprobes in Scanning Probe Microscopy"; Nature 384, 147–151 (1996).

G. Nagy, M. Levy, R. Scarmozzino, R.M. Osgood, Jr. H. Dia, R.E. Smalley, C.A. Michaels, G.W. Flynn and G.F. McLane , "Carbon nanotube tipped atomic force microscopy for measurement of <100 nm etch morphology on semiconductors"; Jul. 27, 1998; American Institute of Physics, Applied Physics Letters, vol. 73, No. 4, pp. 529–531.

S.S. Wong, J.D. Harper, P.T. Lansbury, Jr. and C.M. Lieber, "Carbon Nanotube Tips: High–Resolution Probes for Imaging Biological Systems" J.Am. Chem Soc. 1998, 120, 603–604.

R. M.D. Stevens, N.A. Frederick, B.L. Smith D.E. Morse, G.D.Stucky and P.K. Hansma, "Carbon nanotubes as probes for atomic force microscopy"; 2000 IOP Publishing ltd. Nanotechnology 11 (2000) 1–5. Printed in UK.

* cited by examiner

METHOD OF PRODUCING AN INTEGRATED CIRCUIT WITH A CARBON NANOTUBE

RELATED APPLICATIONS

This patent application claims priority to and all advantages of U.S. Provisional Patent Application Nos. 60/319, 026; 60/319,182; and 60/319,183, which were filed on Dec. 6, 2001; Apr. 12, 2002; and Apr. 12, 2002, respectively.

BACKGROUND OF THE INVENTION

1. Field of the Invention

The subject invention relates to a method of producing an integrated circuit with a carbon nanotube (CNT) for use in the field of nanotechnology.

2. Description of the Related Art

Current related art methods utilize previously prepared carbon nanotubes and manually micro-manipulate the carbon nanotubes into useful structures. The manual manipulation methods include utilizing a modified scanning probe microscope or utilizing electric fields to isolate the carbon nanotubes having desired electric properties. The isolated carbon nanotubes are then selected, removed, and utilized accordingly. Such manual methods are extremely slow and only suitable for the preparation of exploratory test structures, thereby limiting advances in the field of nanotechnology.

SUMMARY OF THE INVENTION AND ADVANTAGES

A method of producing an integrated circuit with a carbon nanotube is disclosed. The integrated circuit includes a source, a drain, and a gate. The source and the drain are positioned on the gate. The method includes the step of depositing a catalytic material onto at least one of the source and the drain. Next, the catalytic material is then subjected to chemical vapor deposition to initiate growth of the carbon nanotube. As such, the carbon nanotube extends from at least one of the source and the drain. The carbon nanotube is then bent toward the integrated circuit such that the carbon nanotube extends between the source and the drain. This renders the integrated circuit operable.

The CNTs of the subject invention exhibit a variety of desired electronic properties. The electronic properties depend on the diameter, number of walls, and defect density of the CNT. The method allows for the CNT to be positioned at specific locations on circuit structures to fulfill specific electronic functions such as forming electric interconnects, diodes and transistors. The subject invention allows for mass production of circuits having CNT connections due to the repeatability of making the circuits functional.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Referring to the Figures, wherein like numerals indicate like or corresponding parts throughout the several views, a method for producing an integrated circuit 12 with a carbon nanotube (CNT) 10 is disclosed. The CNT integrated circuits 12 may be incorporated into any devices, which utilize nanotechnology. These circuits 12 include a plurality of components that are positioned on its surface. In order for the circuits 12 to be functional and incorporated into the devices, the CNT 10 must be connected to at least at two components. The subject invention provides a novel method of connecting the CNT 10 to at least two of these components.

Figure 1:
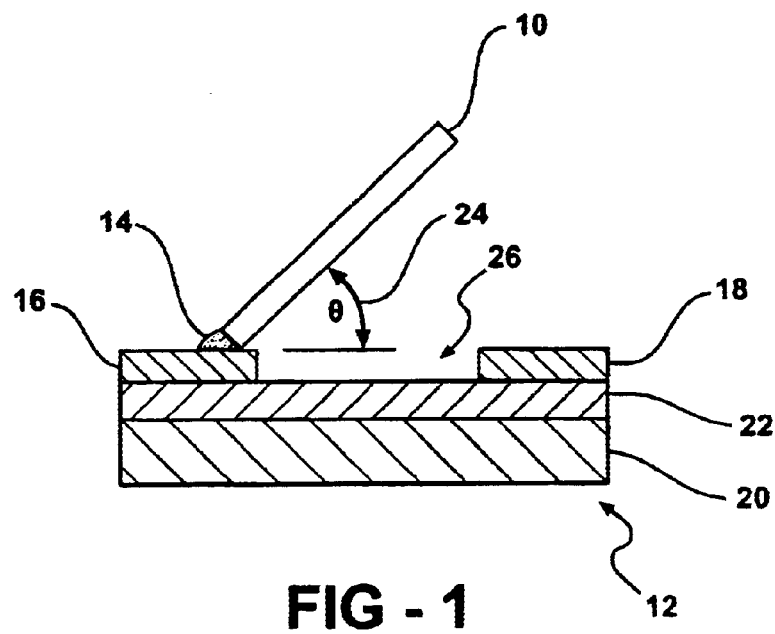
FIG. 1 is a side view of a circuit having components and a carbon nanotube extending from one of the components.

The method includes the steps of depositing a catalytic material, or catalyst, 14 on the circuit 12 in predetermined locations. The circuit 12, as shown in FIG. 1, includes a source 16 and a drain 18 positioned upon a gate 20 coated with a gate oxide 22. Using suitable patterning techniques, the catalytic material 14 is deposited onto at least one of the source 16 and the drain 18. Next, the catalytic material 14 is then subjected to chemical vapor deposition (CVD) to initiate growth of the CNT 10 such that the CNT 10 extends from at least one of the source 16 and the drain 18. The CNT 10 is then bent toward the integrated circuit 12 such that the CNT 10 extends between the source 16 and the drain 18 to render the integrated circuit 12 operable. This bending step is described additionally below.

It is to be understood that the catalyst 14 can be deposited in any location on the integrated circuit 12, including a plurality of locations, where it is needed for fabricating the circuit 12. Preferably, the catalyst 14 is deposited on the source 16 such that the CNT 10 extends from the source 16. However, in alternative embodiments, the catalyst 14 may be deposited on the drain 18 such that the CNT 10 extends from the drain 18. The depositing of the catalyst 14 is carried out using a focused ion beam (FIB) deposition technique or other similar patterning techniques with high resolution. The FIB deposition technique is understood by those skilled in the art. The FIB deposition technique uses an ion beam to deposit the catalyst 14 onto the surface with surgical precision. The catalyst 14 may include, but is not limited to, Ni, Co, Fe, and combinations thereof.

The CNT 10 growth process occurs wherever the catalyst 14 is located on the circuit 12 surface. The growth process enables the preparation of multiple CNTs 10 on the circuit 12 surface simultaneously. Also, multiple circuits 12 may be subject to the growing process simultaneously, thereby making integration and mass production possible.

The CNT 10 can be grown from the catalyst 14 in a straight and directed manner. As shown in FIG. 1, the CNT 10 is grown at a growth angle 24, $\theta$, relative to the position of the source 16. The angle at which the CNT 10 grows relative to the source 16, the drain 18, or both the source 16 and the drain 18 can be controlled. To control this angle, it is possible to apply an electric field as the catalytic material 14 is subjected to CVD. Either a diameter of the CNT 10, or the number of wall present in the CNT 10, or both of these characteristics, can be varied by controlling an amount of the catalytic material 14 that is deposited onto the source 16 and/or the drain 18. Also, if the duration of the CVD is controlled, then the length of the CNT 10 can be varied. A suitable diameter and length of the CNT 10 are selected in order to bridge a gap 26 between the source 16 and the drain 18. For the circuit to function, i.e., operate, the CNT 10 must extend between the source 16 and the drain 18.

One method of growing the CNT 10 is by CVD. CVD is a chemical reaction that transforms gaseous molecules, called precursors, into a solid material, in the form of thin film. Many different precursors may be utilized with the subject invention. Common precursors include, but are not limited to, hydrides, halides, metal-organics such as metal alkyls, metal alkoxides, metal dialkylamides, metal diketonates, or metal carbonyls, and mixtures thereof. For forming the CNT 10, it is understood that the source of carbon may be any organic compound, such as acetylene.

The CVD is carried out in a reactor. Most reactors include gas and vapor delivery lines, a reactor main chamber having a hot wall and a cold wall. The reactor also includes a circuit loading and unloading assembly for positioning the circuit 12 within the reactor.

The reactor also includes at least one energy source. Typical examples of energy sources include resistive heating, radiant heating, and inductive heating. Resistive heating includes energy from a tube furnace or a quartz tungsten halogen lamp. Radiant heating provides energy from radio-frequency and inductive heating provided energy from a laser as a thermal energy source. Yet another energy source is photo energy from an UV-visible light laser.

The products from the CVD include a solid and a gas product. The solid product is the growth of the CNT 10. The gas products are volatile byproducts and are always formed. The gas products generated in CVD processes are usually hazardous and must be disposed of accordingly.

Another type of CVD is plasma enhanced CVD (PECVD). PECVD is performed in a reactor at temperatures up to ~1000° C. The deposited film is a product of a chemical reaction between the source gases supplied to the reactor. A plasma is generated in the reactor to increase the energy available for the chemical reaction at a given temperature. The system for carrying out the PECVD is similar to that described above for CVD.

Figure 2:
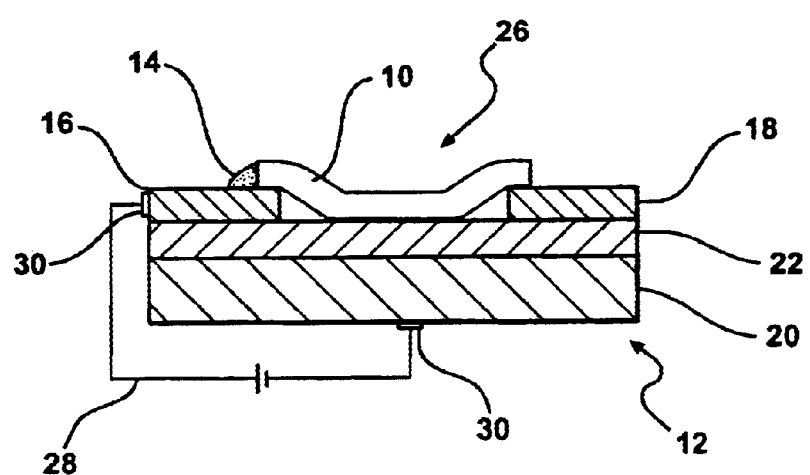
FIG. 2 is a side view of the circuit of FIG. 1 having the carbon nanotube connecting the components, thereby activating the circuit.

The subject invention uses these methods of growing the CNT 10 on the circuit 12 in conjunction with the application of electrostatic forces to form the completed circuit 12. After the CNT 10 has been grown, referring to FIG. 2, the CNT 10 is bent toward the integrated circuit 12 such that the CNT 10 extends between the source 16 and the drain 18 to render the integrated circuit 12 operable. More specifically, the integrated circuit 12 is subjected to an electrical charge. This creates an attractive force between the CNT 10 and the integrated circuit 12. As disclosed in FIG. 2, at least one electrode 30 is positioned on the circuit 12 opposite the CNT 10. In FIG. 2, two electrodes 30 are positioned on the circuit 12. A DC voltage source 28 is used to apply a voltage between the CNT 10 and the single or multiple electrode(s) 30 that have been positioned on the circuit 12 surface opposite the CNT 10. In FIG. 2, the electrodes 30 are positioned below the CNT 10, but this is not required depending on the orientation of the circuit 12. The voltage creates the attractive force between the CNT 10 and the integrated circuit 12 and bend the CNT 10 toward the surface of the circuit 12. The bending of the CNT 10 contacts the other components of the circuit 12, thereby connecting the desired components together and enabling the operation of the circuit 12. Once the CNT 10 is in contact with the other components, the CNT 10 remains connected permanently due to bonding forces between the components and CNT 10. These bonding forces secure the position of the CNT 10 and the connection between the components.

Figure 3:
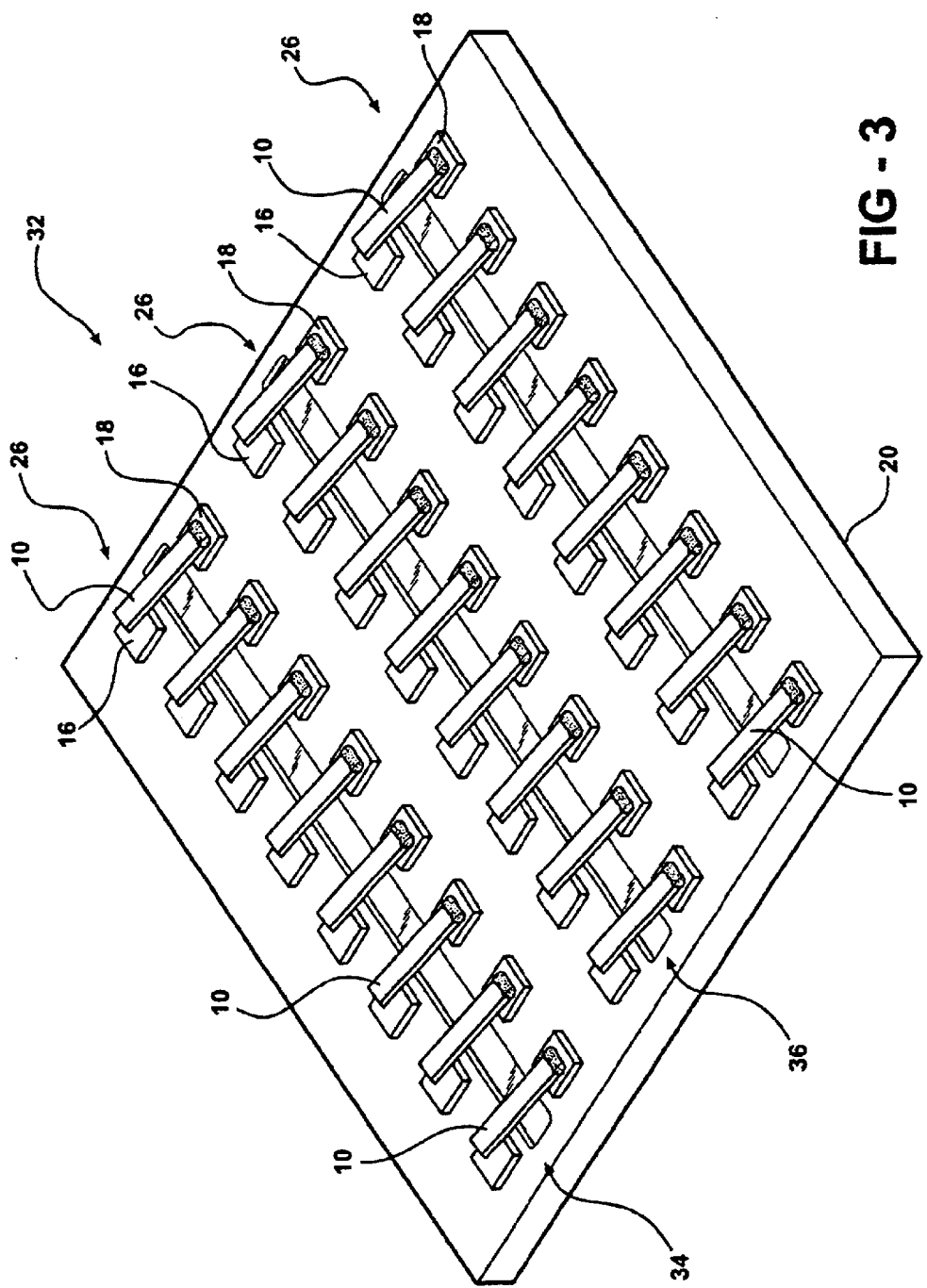
FIG. 3 is a perspective view of a circuit having a plurality of carbon nanotubes aligned in a same direction for forming the circuit.

Referring to FIG. 3, an extended circuit 32 for a device made from utilizing the subject invention is illustrated. The extended circuit 32 is designed to allow for multiple CNTs 10 to be grown and positioned simultaneously. The growth of the CNT 10 is uniform across the entire extended circuit 32 surface due to the principal growth mechanism. The extended circuit 32 may have the electrodes 30 attached similar to that of FIG. 2 and when the voltage 28 is applied all of the CNTs 10 bend and connect with the other components. After all of the CNTs 10 are bent, the gap 26 is bridged between the source 16 and the drain 18. In order for the voltage 28 to be applied, a plurality of electrodes (not shown) may be embedded in the extended circuit 32 for the formation process. With embedded electrodes 30, the formation process occurs independent of the extended circuit 32 operation.

In another embodiment, the formation process occurs according to the design and operation of the extended circuit 32. Therefore, the CNT 10 will be bent down successively as the extended circuit 32 becomes operational, similar to a "domino effect". When the extended circuit 32 is turned on for the first time, a first set 34 of CNTs 10 are bent over to complete the extended circuit 32. The complete extended circuit 32 then causes a second set 36 of CNTs 10 to be bent over. This occurs across the entire extended circuit 32, until the extended circuit 32 is fully operational.

In certain embodiments, it may be desirable to increase the rigidity of the CNT 10 that extends from the source 16, the drain 18, or both 16, 18. To accomplish this, it is preferred that a suitable material, such as platinum, is deposited onto at least one of the source 16 and the drain 18 prior to deposition of the catalytic material 14. The platinum enhances the mechanical attachment of the CNT 10 to the source 16 and/or the drain 18 and enhance the lifetime of the CNT 10 in the circuit 12. Preferably, the platinum is deposited using FIB deposition techniques.

Obviously, many modifications and variations of the present invention are possible in light of the above teachings. The invention may be practiced otherwise than as specifically described within the scope of the appended claims.

What is claimed is:

1. A method of producing an integrated circuit with a carbon nanotube, wherein the integrated circuit includes a source, a drain, and a gate, the source and drain being positioned on the gate, said method comprising the steps of:

depositing a catalytic material onto at least one of the source and the drain;

subjecting the catalytic material to chemical vapor deposition to initiate growth of the carbon nanotube such that the carbon nanotube extends from at least one of the source and the drain;

depositing platinum onto at least one of the source and the drain prior to deposition of the catalytic material to increase the rigidity of the carbon nanotube that extends from at least one of the source and the drain; and bending the carbon nanotube toward the integrated circuit such that the carbon nanotube extends between the source and the drain to render the circuit operable.

2. A method as set forth in claim 1 wherein the step of bending the carbon nanotube is further defined as subjecting the integrated circuit to an electrical charge to create an attractive force between the carbon nanotube and the integrated circuit.

3. A method as set forth in claim 2 wherein the step of subjecting the integrated circuit to the electrical charge comprises the step of positioning at least one electrode on the circuit opposite the carbon nanotube.

4. A method as set forth in claim 3 wherein the step of subjecting the integrated circuit to an electrical charge further comprises the step of applying a voltage between the carbon nanotube and the at least one electrode to create the attractive force between the carbon nanotube and the integrated circuit.

5. A method as set forth in claim 1 wherein the step of depositing the catalytic material onto at least one of the source and the drain is further defined as depositing the catalytic material onto the source.

6. A method as set forth in claim 5 wherein the step of subjecting the catalytic material to chemical vapor deposition is further defined as subjecting the catalytic material to chemical vapor deposition to initiate growth of the carbon nanotube such that the carbon nanotube extends from the source.

7. A method as set forth in claim 1 wherein the step of depositing the catalytic material onto at least one of the source and the drain is further defined as depositing the catalytic material onto the drain.

8. A method as set forth in claim 7 wherein the step of subjecting the catalytic material to chemical vapor deposition is further defined as subjecting the catalytic material to chemical vapor deposition to initiate growth of the carbon nanotube such that the carbon nanotube extends from the drain.

9. A method as set forth in claim 1 wherein the step of depositing the catalytic material onto at least one of the source and the drain is further defined as depositing a catalytic material selected from the group consisting of nickel, cobalt, iron, and combinations thereof.

10. A method as set forth in claim 1 wherein the step of subjecting the catalytic material to chemical vapor deposition comprises the step of transforming a gaseous precursor selected from the group consisting of hydrides, halides, metal-organics, and combinations thereof into a solid material.

11. A method as set forth in claim 1 wherein the step of subjecting the catalytic material to chemical vapor deposition is further defined as subjecting the catalytic material to plasma enhanced chemical vapor deposition.

12. A method as set forth in claim 1 wherein the step of depositing the catalytic material onto at least one of the source and the drain is further defined as depositing the catalytic material onto at least one of the source and the drain using focused ion beam deposition.

13. A method as set forth in claim 1 further comprising the step of controlling an angle that the carbon nanotube grows at relative to at least one of the source and the drain.

14. A method as set forth in claim 13 wherein the step of controlling the angle that the carbon nanotube grows at is further defined as applying an electric field as the catalytic material is subjected to chemical vapor deposition.

15. A method as set forth in claim 1 wherein the step of depositing the catalytic material onto at least one of the source and the drain comprises the step of controlling an amount of the catalytic material that is deposited onto at least one of the source and the drain to vary at least one of a diameter of the carbon nanotube and a number of walls present in the carbon nanotube.

16. A method as set forth in claim 1 wherein the step of subjecting the catalytic material to chemical vapor deposition comprises the step of controlling a duration of the chemical vapor deposition to vary a length of the carbon nanotube.

17. A method as set forth in claim 1 wherein the step of depositing platinum onto at least one of the source and the drain is further defined as depositing platinum onto at least one of the source and the drain using focused ion beam deposition.

* * * * *